United States Patent
Tanaka et al.

(10) Patent No.: US 10,687,694 B2
(45) Date of Patent: Jun. 23, 2020

(54) WIRE-DRIVEN MANIPULATOR

(71) Applicant: Canon U.S.A. Inc., Melville, NY (US)

(72) Inventors: Yusuke Tanaka, Tokyo (JP); Ichiro Okumura, Abiko (JP)

(73) Assignee: Canon U.S.A., Inc., Melville, NY (US)

(*) Notice: Subject to any disclaimer, the term of this patent is extended or adjusted under 35 U.S.C. 154(b) by 165 days.

(21) Appl. No.: 15/953,245

(22) Filed: Apr. 13, 2018

(65) Prior Publication Data

US 2018/0310804 A1 Nov. 1, 2018

Related U.S. Application Data

(60) Provisional application No. 62/491,826, filed on Apr. 28, 2017.

(51) Int. Cl.
*A61B 1/005* (2006.01)
*F16H 19/06* (2006.01)

(52) U.S. Cl.
CPC .......... *A61B 1/0057* (2013.01); *A61B 1/0055* (2013.01); *F16H 19/0645* (2013.01); *F16H 2019/0695* (2013.01)

(58) Field of Classification Search
CPC .............................. A61B 1/0055; A61B 1/0057
See application file for complete search history.

(56) References Cited

U.S. PATENT DOCUMENTS

| | | | |
|---|---|---|---|
| 4,700,693 A * | 10/1987 | Lia ...................... | A61B 1/0055 356/241.4 |
| 9,144,370 B2 * | 9/2015 | Kato ...................... | A61B 1/008 |
| 10,413,289 B2 * | 9/2019 | Cabrera ........... | A61B 17/00234 |
| 2001/0053874 A1 * | 12/2001 | Pauker ................. | A61B 1/0055 600/152 |
| 2003/0036748 A1 * | 2/2003 | Cooper ............ | A61B 17/00234 606/1 |
| 2004/0225186 A1 * | 11/2004 | Horne, Jr. .......... | A61B 1/00071 600/139 |
| 2007/0221701 A1 * | 9/2007 | Ortiz .................... | A61B 17/068 227/175.1 |
| 2008/0194911 A1 * | 8/2008 | Lee ...................... | A61B 1/0055 600/109 |
| 2009/0234186 A1 * | 9/2009 | Lin ....................... | A61B 1/0055 600/113 |
| 2013/0131450 A1 * | 5/2013 | Surti .................. | A61B 1/00135 600/114 |
| 2018/0042452 A1 * | 2/2018 | Okada .................... | A61B 1/008 |

* cited by examiner

*Primary Examiner* — Terence Boes
(74) *Attorney, Agent, or Firm* — Canon U.S.A., Inc., IP Division

(57) ABSTRACT

A linear-member-driven manipulator is provided that includes a bendable member that is bendable along a bending plane and includes a plurality of bendable portions; a linear member used to bend at least one of the bendable portions; a plurality of guiding members that guide the linear member that is driven; and a plurality of support members, each support member extending from one of the guiding members to the bendable member, wherein each guiding member is swingable with respect to the bendable member; and wherein, for each support member, a projection distance between the linear member and the support member on the bending plane is greater than or equal to a projection distance between the linear member and a bending neutral line of the bendable member on the bending plane.

16 Claims, 7 Drawing Sheets

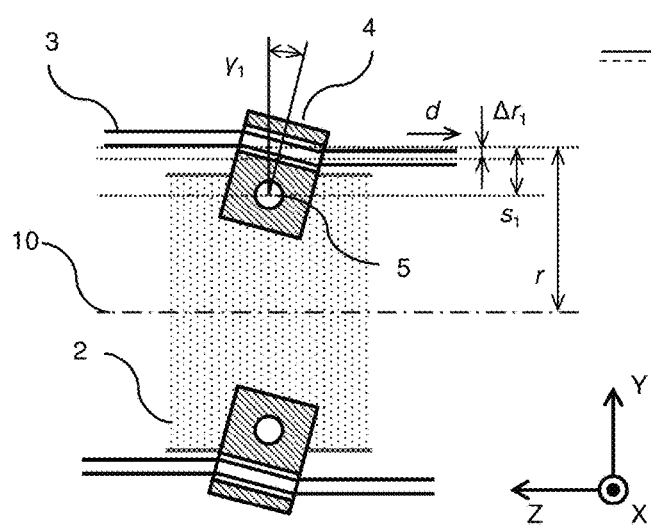
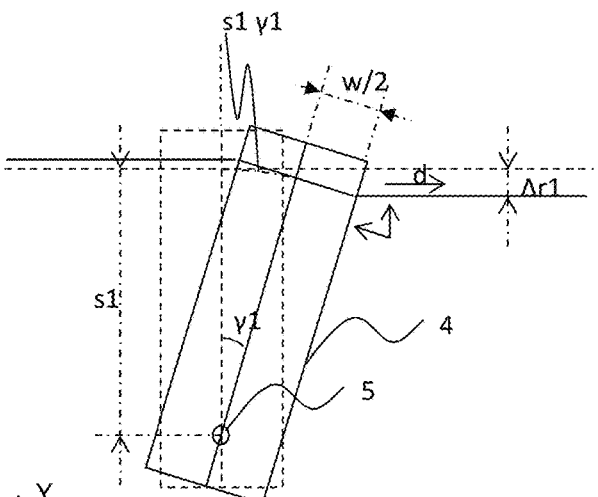
Fig. 5(A)
Fig. 5(B)
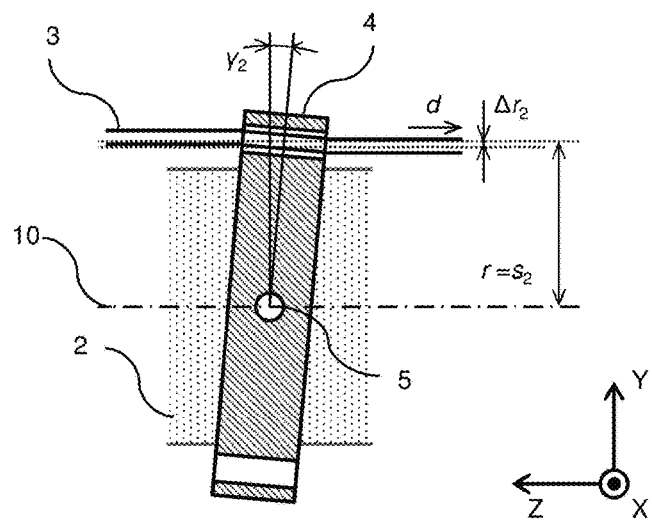
Fig. 6

WIRE-DRIVEN MANIPULATOR

CROSS-REFERENCE TO RELATED APPLICATION(S)

This application relates, and claims priority, to U.S. Provisional Application Ser. No. 62/491,826, filed Apr. 28, 2017, the entire disclosure of which is incorporated by reference herein in its entirety.

BACKGROUND OF THE INVENTION

Field of the Invention

The present disclosure relates to the structure of a flexible portion of an endoscope.

Description of the Related Art

Endoscopes are medical devices used to examine or treat areas inside the body. Endoscopes are classified into rigid endoscopes and flexible endoscopes. A flexible endoscope includes a bendable portion, which undergoes a bending operation, at a distal end portion thereof that is inserted into the body. Japanese Utility Model Laid-Open No. 51-154084 discloses a structure of a bendable portion of a flexible endoscope. In this structure, a plurality of joint rings are rotatably connected to each other. The group of joint rings can be tilted by pulling wires that are fixed to the joint ring at the distal end. The joint rings may be connected to each other by using rivets so as to be rotatable around the rivets as disclosed in Japanese Patent Laid-Open No. 3-68326 and Japanese Patent Laid-Open No. 2003-135381, or be formed integrally with each other with elastic connecting portions provided therebetween as disclosed in Japanese Patent Laid-Open No. 2007-82815.

Japanese Patent Laid-Open No. 2011-56074 and Japanese Patent Laid-Open No. 2011-143173 disclose a structure of members that support wires for pulling the joint ring structure. According to Japanese Patent Laid-Open No. 2011-56074 and Japanese Patent Laid-Open No. 2011-143173, the bendable portion can be smoothly bent and wear of the wires can be reduced by reducing the sliding resistance between the wire that is pulled to bend the bendable portion and the wire-supporting members. Japanese Patent Laid-Open No. 2011-56074 discloses a mechanism for making each wire-supporting member slide along the bendable portion to reduce the normal force applied to each wire and reduce friction accordingly. Japanese Patent Laid-Open No. 2011-143173 discloses a mechanism for making each wire-supporting member move relative to the bendable portion to reduce friction. In these structures, the distance from the neutral line of the bendable portion in the longitudinal direction to each wire before the sliding or moving operation differs from that after the sliding or moving operation. To estimate the bent shape of the bendable portion, the curvature of the bendable portion is calculated on the basis of the relationship between the amount by which each wire is driven and the distance from the neutral line to the wire. Therefore, a change in the distance from the neutral line to each wire leads to an error during orientation control based on the estimation of the bent shape of the bendable portion.

SUMMARY OF THE INVENTION

The present disclosure provides a wire-driven manipulator that is advantageous in increasing accuracy when the orientation of a bendable portion is estimated and controlled on the basis of the amount by which a wire is driven.

According to the present disclosure, a linear-member-driven manipulator includes a bendable member that is bendable along a bending plane and includes a plurality of bendable portions; a linear member used to bend at least one of the bendable portions; a plurality of guiding members that guide the linear member that is driven; and a plurality of support members, each support member extending from one of the guiding members to the bendable member, wherein each guiding member is swingable with respect to the bendable member; and wherein, for each support member, a projection distance between the linear member and the support member on the bending plane is greater than or equal to a projection distance between the linear member and a bending neutral line of the bendable member on the bending plane.

Further features of the present invention will become apparent from the following description of exemplary embodiments with reference to the attached drawings.

BRIEF DESCRIPTION OF THE DRAWINGS

FIG. 5(A) is a conceptual diagram illustrating a change in the orientation of a guiding member according to the related art at the time when a linear member is driven. FIG. 5(B) is a conceptual diagram illustrating the changing orientation of one guiding member where the changes are illustrated with dashed lines.

FIG. 6 is a conceptual diagram illustrating a change in the orientation of the guiding member at the time when the linear member is driven.

DESCRIPTION OF THE EMBODIMENTS

Figure 1:
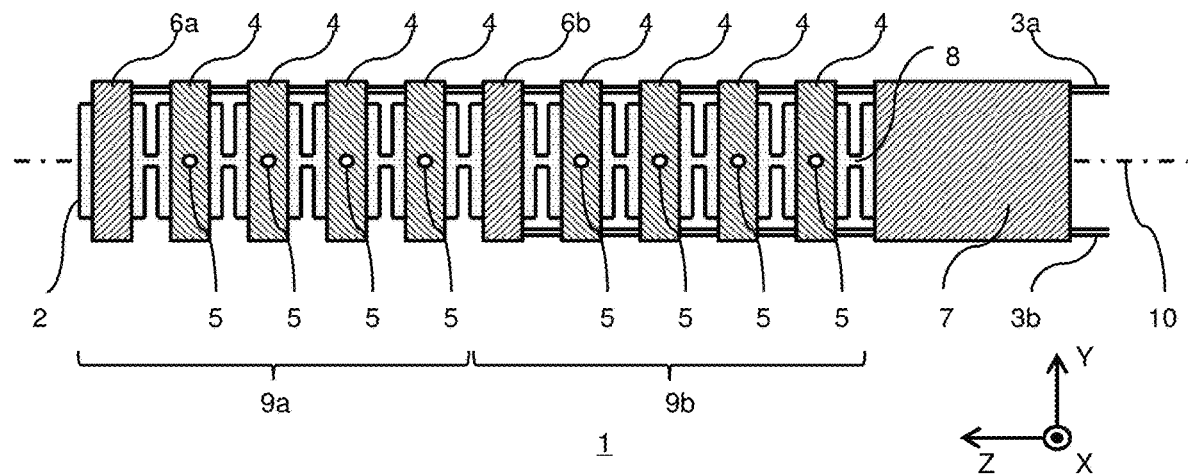
FIG. 1 is a front view illustrating the structure of a wire-driven manipulator according to an embodiment of the present disclosure.

An embodiment of the present disclosure will be described with reference to the drawings. A wire-driven manipulator according to the embodiment of the present disclosure will be described. FIG. 1 is a front view illustrating the structure of a wire-driven manipulator 1 according to the present embodiment. The wire-driven manipulator 1 includes a bendable member 2, linear members 3 (e.g., 3a and 3b), guiding members 4, support members 5, distal end members 6a and 6b, and a base portion 7.

The bendable member 2 has a tubular shape having a center axis extending in the Z-axis direction, and is bendable along the YZ plane due to elastic connecting portions 8. The bendable member 2 is fixed to a base portion 7. The elastic connecting portions 8 are part of the bendable member and are formed or designed so as to have the structure of an elastic hinge by forming slits in the bendable member 2. Although the bendable member 2 is bendable only along the YZ plane in FIG. 1, the bendable member 2 may instead be capable of performing three-dimensional deformation including deformation along the XZ plane. In these cases, the bendable member 2 is often made of a shape-memory alloy that serves as a super-elastic material. The bendable member 2 may instead have a bendable structure formed by, for example, connecting multiple members with rivets or the like so that the multiple members are rotatable around the rivets.

The bendable member 2 includes a plurality of bendable sections 9 (e.g., 9a and 9b) that are individually bendable. The distal end members 6a and 6b, to which the linear members 3a and 3b are fixed, are respectively provided at the distal ends of the bendable sections 9a and 9b. The guiding members 4, which guide the linear members 3a and 3b that are driven, are arranged in each of the bendable sections. The distal end members 6a and 6b are fixed to the bendable member 2 by using, for example, adhesive, pins, or screws. Alternatively, the distal end members 6a and 6b may be formed integrally with the bendable member 2. The guiding members 4, may be concentric rings located outside but proximal to a tube-shaped bending member 2.

At least one or more linear members 3 are provided for each bendable section 9. The linear members 3 are made of synthetic fiber, such as nylon, or metal wires, such as piano wires. In the present embodiment, it is assumed that metal wires are used.

Figure 2:
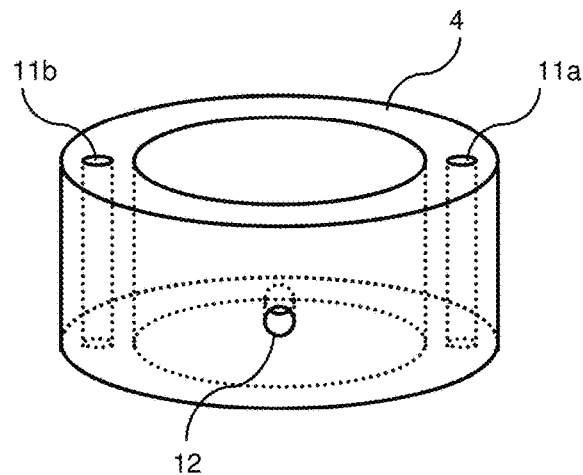
FIG. 2 is a perspective view of a guiding member.

FIG. 2 is a perspective view illustrating a guiding member 4. The guiding member 4 is a tubular member having guide holes 11a and 11b that guide the linear members 3a and 3b. The guiding member 4 is arranged so that the bendable member 2 extends through the tubular portion thereof, and is supported in such a manner that a pin-shaped support member 5 is inserted through a support hole 12 and a fitting hole formed in the bendable member 2. The guiding member 4 enables the linear members 3a and 3b to be driven without buckling while being maintained parallel to the center axis of the bendable member 2. The guiding member 4 is in contact with the linear members 3a and 3b in the guide holes 11a and 11b, and is, therefore, made of a material having a small coefficient of friction, such as a resin. Although two bendable sections 9 are illustrated in FIG. 1, the numbers of bendable sections 9 and guiding members 4 may be any number depending on the usage. For example, there may be three bendable sections or four bendable sections. Similarly, although FIG. 1 shows bendable sections 9a and 9b having the same length, the bendable sections may bendable sections may each have a different length, which may be dependent upon intended application. Although the guiding members 4 and the support members 5 are separate components in the present embodiment, they may instead be integrated with each other.

Figure 3:
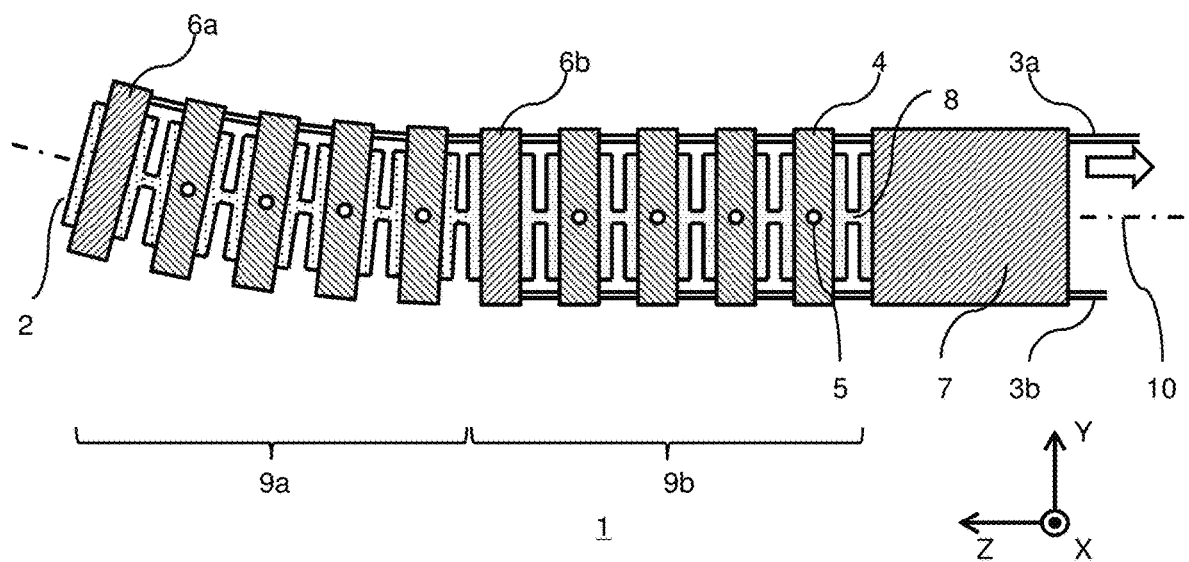
FIG. 3 is a front view illustrating the manner in which the wire-driven manipulator is deformed when a linear member is driven.
Figure 4:
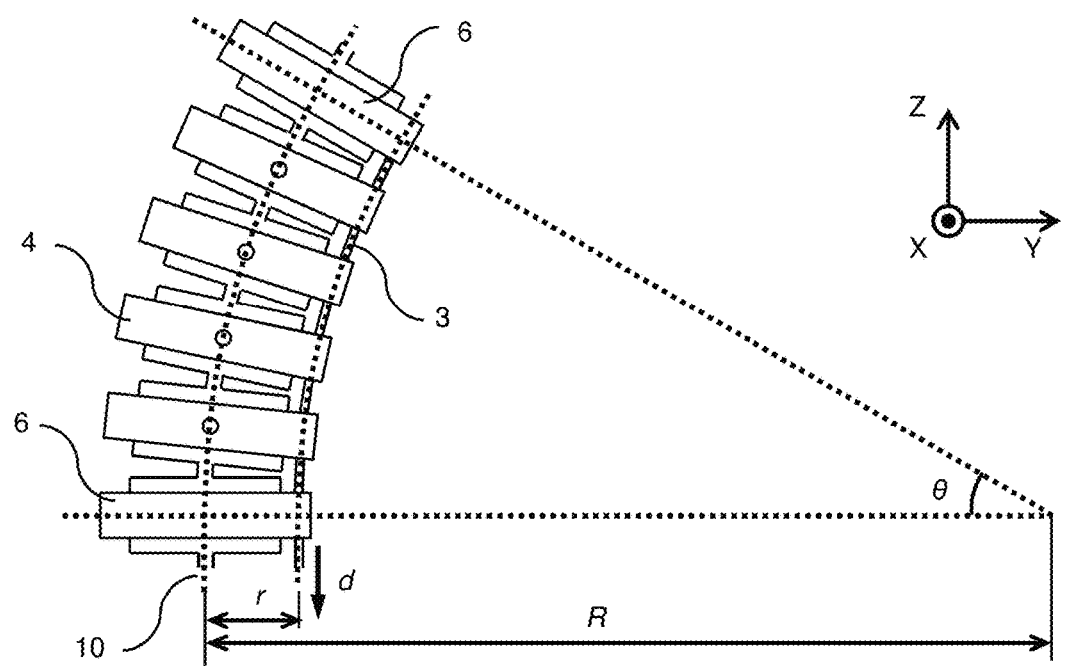
FIG. 4 is a conceptual diagram illustrating the manner in which the wire-driven manipulator is deformed when the linear member is driven.

The driving operation of the wire-driven manipulator will be described with reference to FIG. 3. When the linear member 3a is driven in the −Z direction by a drive mechanism (not shown) provided at an end opposite to the end at which the distal end member 6a is provided, a portion of the distal end member 6a that is connected to the linear member 3a is pulled in the −Z direction. Since the length of the center line 10 of the bendable member 2 does not change, the bendable section 9a of the bendable member 2 is deformed in the +Y direction. When the rigidity of the bendable member 2 is uniform in each bendable section 9, the bendable section 9a is bent into an arc shape having a constant curvature. The center line 10 of the bendable member 2 is bent along a single plane in each bendable section 9. This plane is defined as a bending plane of each bendable section 9. In FIG. 3, all of the bendable sections 9 have the same bending plane. In the case where the bendable member 2 is three-dimensionally deformable, the bendable sections 9 have different bending planes. FIG. 4 illustrates bending deformation along the YZ plane caused by driving the linear member 3 fixed to the distal end member 6 of the $N^{th}$ bendable section 9 from the base portion 7. In the equations below, d denotes the amount by which the linear member 3 is driven, r denotes the distance between the bendable-member center line 10 and the linear member 3 in the radial direction, R denotes the radius of curvature in the driven state, L is the length of the bendable-member center line 10 in the bendable section 9, and θ denotes the relative angle between the $N^{th}$ and $N-1^{th}$ distal end members 6. The following relationships are satisfied:

$$R \cdot \theta = L \quad (1)$$

$$(R-r) \cdot \theta = L - d \quad (2)$$

The following equation can be derived from Equations (1) and (2):

$$\theta = d/r \quad (3)$$

This shows that, when the orientation of each distal end member 6 is controlled on the basis of the amount d by which the linear member 3 is driven, the distance r between the bendable-member center line 10 and the linear member 3 in the radial direction is preferably constant. A change in the distance r leads to an orientation error of each distal end member 6.

FIG. 5(A), FIG. 5(B), and FIG. 6 are conceptual diagrams illustrating a change in the orientation of the guiding member 4 that occurs when the linear member 3 is driven. The influence of the structures of the guiding member 4 and the support member 5 on the distance r between the bendable-member center line 10 and the linear member 3 in a radial direction will be described with reference to FIG. 5(A) and FIG. 6. In each of the structures illustrated in FIG. 5(A) and FIG. 6, the guiding member 4 is connected to the bendable member 2 by the support member 5 so as to be rotatable around an axis parallel to the X-axis. Since the guiding member 4 rotates, the resistance due to friction between the guiding member 4 and the linear member 3 can be reduced.

FIG. 5(A) illustrates the structure around the guiding member 4 in a common linear-member-driven manipulator according to the related art. The support member 5 of the guiding member 4 is located near the linear member 3. The bendable member 2 is bent along the YZ plane. Here, r denotes the projection distance between the bendable-member center line 10 and the linear member 3 on the bending plane (YZ plane), and $s_1$ denotes the distance between the linear member 3 and the support member 5 along the bending plane.

In FIG. 5(B) the position of the guiding member 4 prior to the driving of linear member 3 is shown with the dotted lines. The solid lines in FIG. 5(B) illustrate the position of guiding member 4 after linear member 3 has been driven d distance in the −z direction. The center line of linear member 3 before the change in position of the guiding member 4 is represented by the top dotted line, and the center line of linear member 3 after linear member 3 has been driven d distance is illustrated by the solid line that starts above the top dotted line and descends to below the same dotted line.

Assume that, when the linear member 3 is driven in the −Z direction by the distance d, the guiding member 4 is moved so as to follow the linear member 3 due to the friction between the linear member 3 and the guiding member 4. In this case, the amount of movement of the linear member 3($d$) is equal to $s_1 * \gamma_1$. Therefore, the amount of rotation $\gamma_1$ of the guiding member 4 around the X-axis can be calculated as follows:

$$\gamma_1 = d/s_1 \quad (4)$$

When w denotes the thickness of the guiding member 4 in the Z-axis direction, and when $\gamma$ is sufficiently small such that $\sin \gamma_1$ can be assumed as $\gamma_1$, the displacement $\Delta r_1$ of the guiding member 4 in the Y-axis direction can be calculated as follows:

$$\Delta r_1 = \gamma_1 \cdot w/2 = w \cdot d/(2 \cdot s_1) \quad (5)$$

FIG. 6 illustrates the structure around the guiding member 4 in the linear-member-driven manipulator according to the present disclosure. The support member 5 of the guiding member 4 is disposed on the bendable-member center line. Similar to the structure illustrated in FIG. 5(A), the bendable member 2 is bent along the YZ plane. When r denotes the projection distance between the bendable-member center line 10 and the linear member 3 on the bending plane (YZ plane) and $s_2$ denotes the projection distance between the linear member 3 and the support member 5 on the bending plane, similar to the case described above with reference to FIG. 5(A), the amount of rotation $\gamma_2$ and the displacement $\Delta r_2$ of the guiding member 4 in the Y-axis direction can be calculated as follows:

$$\gamma_2 = d/s_2$$

$$\Delta r_2 = w \cdot d/(2 \cdot s_2) \quad (7)$$

As described above, a change in the projection distance r between the bendable-member center line 10 and the linear member 3 on the bending plane causes an orientation error of the distal end member 6. Therefore, $\Delta r$ is preferably as small as possible from the viewpoint of orientation control. Comparison between the structures of the guiding member 4 and the support member 5 in FIG. 5(A) and those in FIG. 6 shows that the following relationship is satisfied:

$$s_1 < s_2 \quad (8)$$

Accordingly, the following expression is satisfied:

$$\Delta r_1 > \Delta r_2 \quad (9)$$

Thus, as the distance between the support member 5 and the linear member 3 increases, the radius of rotation of the guiding member 4 increases and the orientation error can be reduced. The radius of rotation of the guiding members 4 is, for example, preferably greater than or equal to the projection distance r between the bendable-member center line 10 and the linear member 3 on the bending plane.

The above description is based on the assumption that the linear member 3 is on the bending plane. However, the linear member 3 is not necessarily on the bending plane. In the case where the linear member 3 is not on the bending plane, the location of the linear member 3 projected onto the bending plane may satisfy the above-described relationship.

The structure and function of the support member 5 will now be described with reference to FIG. 7 and FIG. 8.

Figure 7:
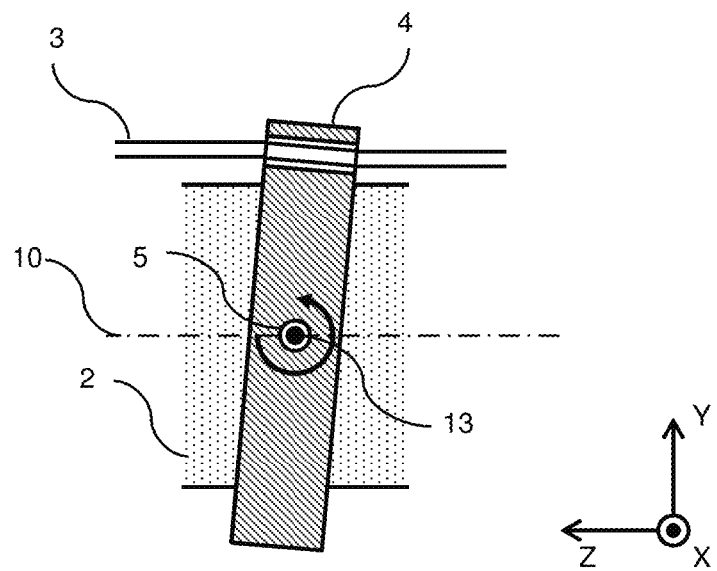
FIG. 7 is a conceptual diagram illustrating the arrangement and function of a support member.

FIG. 7 is a front view of a region around the support member 5. The guiding member 4 is rotatable around an axis that is parallel to the X-axis and that passes through a rotation center 13. The support member 5 is, for example, a mechanism including a bearing that enables rotation around the axis parallel to the X-axis. Alternatively, the support member 5 may be pin-shaped so as to be slidable with respect to at least one of the bendable member 2 and the guiding member 4, and be rotatable around the axis parallel to the X-axis. Alternatively, the support member 5 may instead be made of a super-elastic material, such as rubber and be fixed to both the bendable member 2 and the guiding member 4 so as to enable the support member 5 to be twisted around the axis parallel to the X-axis. Alternatively support member 5 may instead be bendable in a hinge motion along an axis parallel to the bending plane.

Figure 8:
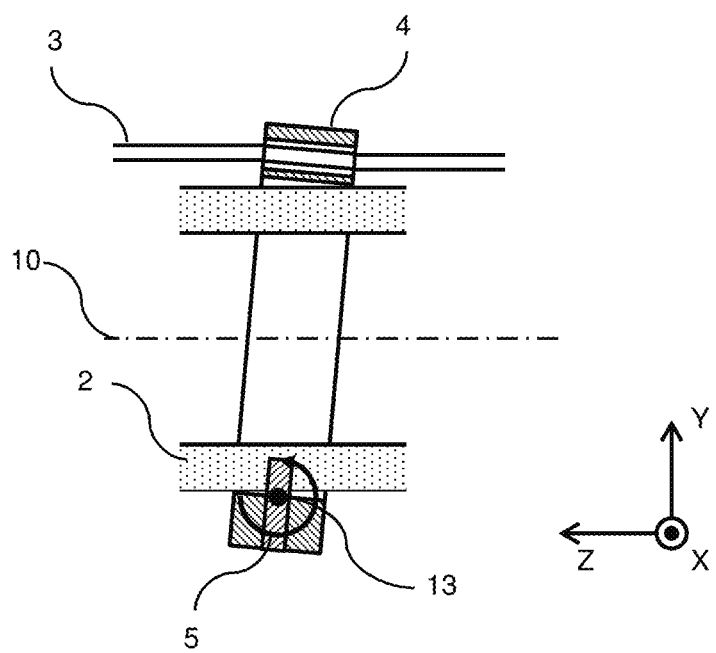
FIG. 8 is a conceptual diagram illustrating the arrangement and function of a support member.

FIG. 8 is a sectional view of the region around the support member 5. As described above with reference to FIG. 7, the guiding member 4 is rotatable around the axis that is parallel to the X-axis and that passes through the rotation center 13. The support member 5 is provided with, for example, a link mechanism that enables the support member 5 to rotate around the axis parallel to the X-axis. Alternatively, the support member 5 may be composed of a structure or material that is flexible in the Z-axis direction.

In the case where the support member 5 is twistable or flexible, the guiding member 4 rotates so as to follow the linear member 3 due to friction when the linear member 3 is driven by a small amount. When the linear member 3 is driven by a large amount, the guiding member 4 slides along the linear member 3, so that the amount of rotation of the guiding member 4 can be reduced. Accordingly, the amount of change in the projection distance r between the bendable-member center line 10 and the linear member 3 on the bending plane (YZ plane) can be reduced, and the orientation control error of the bendable member 2 that occurs when the linear member 3 is driven can be reduced. The support member 5 may be structured so as to be both twistable and flexible.

FIRST EXAMPLE

Figures 9A, 9B:
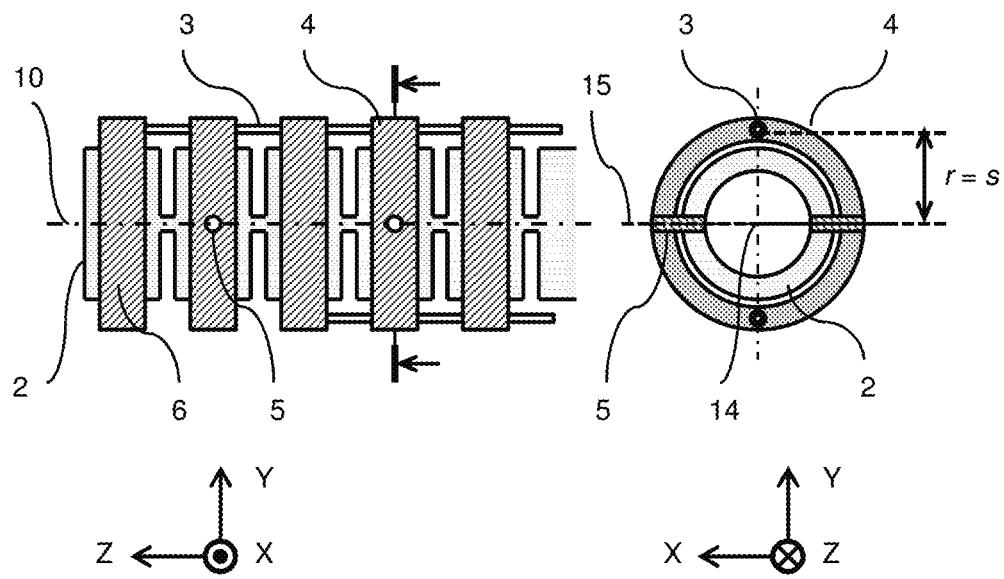
FIG. 9(A) illustrates is a first example of the present disclosure.
FIG. 9(B) is a sectional view of FIG. 9(A) at the marked line.

Referring to FIG. 9, an arrangement of the linear member 3, the guiding members 4, and the support members 5 according to a first example of the present disclosure will be described.

The left side of FIG. 9 shows a front view of a region around the guiding members 4. The right side of FIG. 9 shows a sectional view taken along the XY plane. The bendable section 9 of the bendable member 2 has the YZ plane as the bending plane thereof. The support members 5 are twistable or rotatable around an axis parallel to the X-axis. When r denotes the distance between a bendable-member center 14 and the linear member 3 projected onto the bending plane and s denotes the distance between the linear member 3 and the rotation center axis 15 of the support members 5, the following equation is satisfied:

$$r = s \quad (10)$$

SECOND EXAMPLE

Figures 10A, 10B:
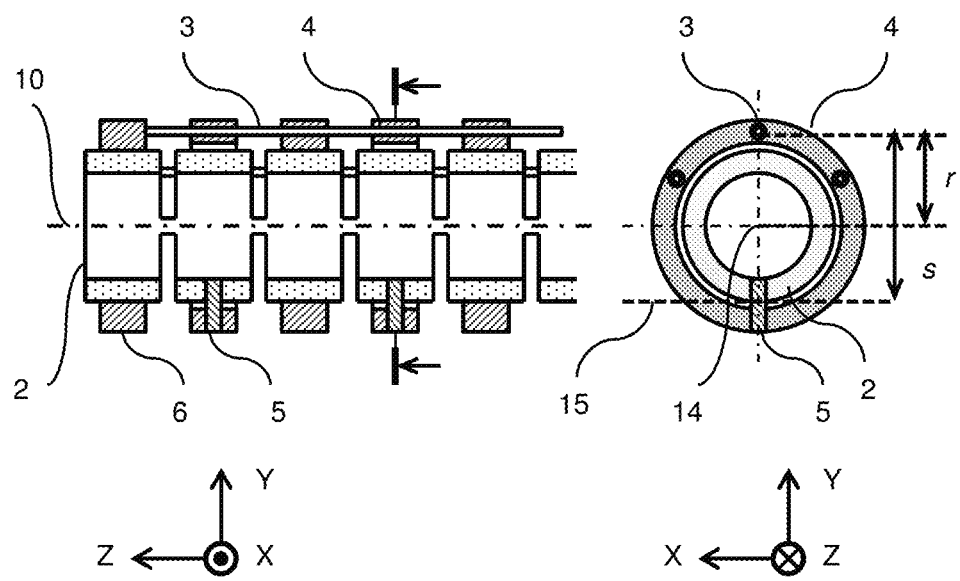
FIG. 10(A) illustrates a second example of the present disclosure.
FIG. 10(B) is a sectional view of FIG. 10(A) at the marked line.

Referring to FIG. 10, an arrangement of the linear member 3, the guiding members 4, and the support members 5 according to a second example of the present disclosure will be described.

The left side of FIG. 10 shows a sectional view of a region around the guiding members 4 taken along the YZ plane. The right side of FIG. 10 shows a sectional view taken along the XY plane. The bendable section 9 of the bendable member 2 has the YZ plane as the bending plane thereof. The support members 5 are flexible and are bendable in the Z-axis direction to enable the guiding members 4 to rotate around an axis 15 parallel to the X-axis. In this case, r and s satisfy the following relationship:

$$r<s \qquad (11)$$

THIRD EXAMPLE

Figures 11A, 11B, 11C:
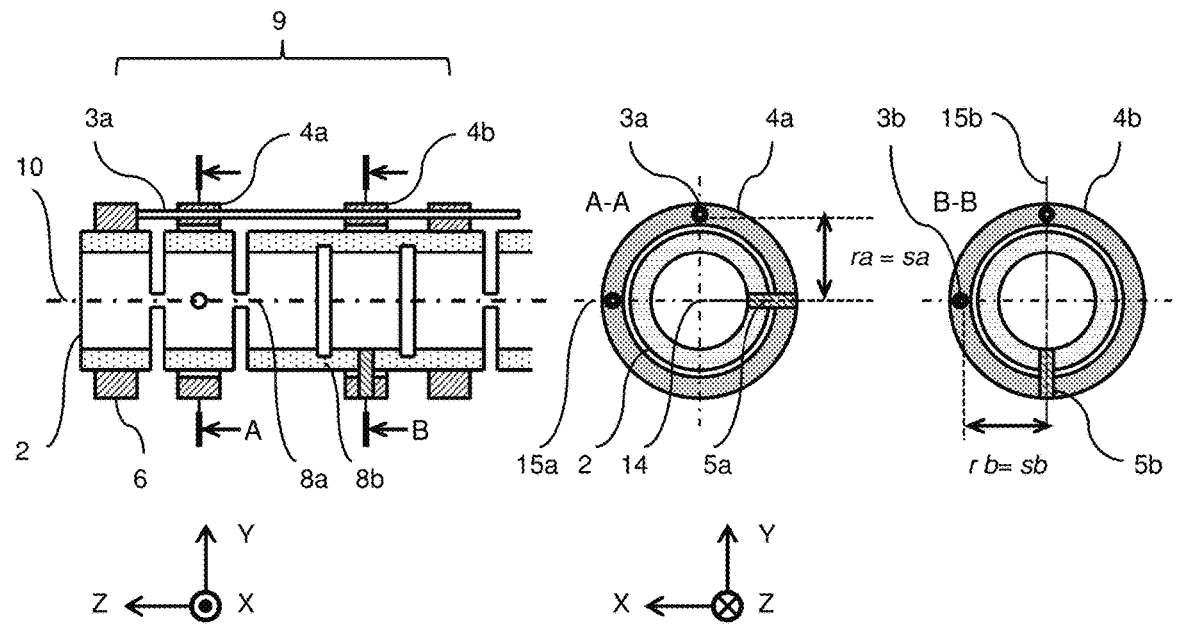
FIG. 11(A) illustrates a third example of the present disclosure.
FIG. 11(B) and FIG. 11(C) are sectional views of FIG. 11(A) at the positions A-A and B-B, respectively.

Referring to FIG. 11, an arrangement of the linear members 3, the guiding members 4, and the support members 5 according to a third example of the present disclosure will be described. In each of the first and second examples, the linear-member-driven manipulator 2 is bent along a plane. In contrast, in the present example, the linear members 3, the guiding members 4, and the support members 5 are arranged so that the linear-member-driven manipulator 2 is three-dimensionally bendable.

The left side of FIG. 11 shows a sectional view of the region around the guiding members 4 taken along the YZ plane. The right side of FIG. 11 shows sectional views taken along lines A-A and B-B. Referring to the left side of FIG. 11, in a single bendable section 9 of the bendable member 2, elastic connecting portions are alternately disposed at locations that are shifted from each other by 90 degrees around the bendable-member center line 10. Accordingly, the bendable member 2 is bendable along two planes, that is, along the YZ plane in the regions around the guiding members 4a, and along the XZ plane in the regions around the guiding members 4b. A linear member 3a is provided to bend the bendable member 2 along the YZ plane, and a linear member 3b is provided to bend the bendable member 2 along the XZ plane. The linear members 3a and 3b are both fixed to the same distal end member 6.

In the sectional view taken along line A-A, the guiding member 4a is supported by the support member 5a. The support member 5a is twistable around a rotation center axis 15a that is parallel to the X-axis. The distance ra between the bendable-member center 14 and the linear member 3a and the distance sa between the linear member 3a and the rotation center axis 15a of the support member 5a satisfy the following relationship:

$$ra=sa \qquad (12)$$

Similarly, in the sectional view taken along line B-B, the support member 5b is twistable, and the distance rb between the bendable-member center 14 and the linear member 3b and the distance sb between the linear member 3b and a rotation center axis 15b of the support member 5b satisfy the following relationship:

$$rb=sb \qquad (13)$$

FOURTH EXAMPLE

Figures 12A, 12B, 12C:
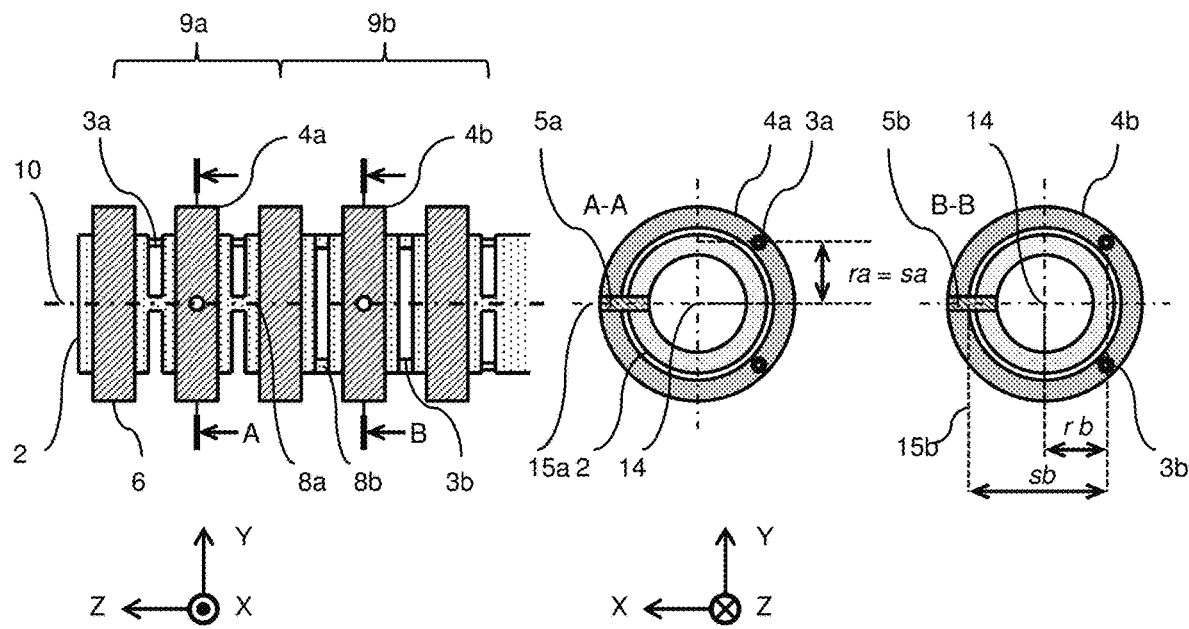
FIG. 12(A) illustrates a fourth example of the present disclosure.
FIG. 12(B) and FIG. 12(C) are sectional views of FIG. 12(A) at the positions A-A and B-B, respectively.

Referring to FIG. 12, an arrangement of the linear members 3, the guiding members 4, and the support members 5 according to a fourth example of the present disclosure will be described.

The left side of FIG. 12 shows a front view of the region around the guiding members 4. The right side of FIG. 12 shows sectional views taken along lines A-A and B-B.

Referring to the left side of FIG. 12, the bendable member 2 includes bendable sections 9 having different bending planes. In the bendable section 9a, elastic connecting portions 8a are arranged on the XZ plane so that the bendable member 2 is bendable along the YZ plane. In the bendable section 9b, elastic connecting portions 8b are arranged on the YZ plane so that the bendable member 2 is bendable along the XZ plane.

In the sectional view taken along line A-A, the guiding member 4a is supported by the support member 5a that is twistable around a rotation center axis 15a. The distance ra between the bendable-member center 14 and the linear member 3a and the distance sa between the linear member 3a and the rotation center axis 15a of the support member 5a satisfy the following relationship:

$$ra=sa \qquad (14)$$

In the sectional view taken along line B-B, the guiding member 4b is supported by the support member 5b that is flexible around a rotation center axis 15b. The distance rb between the bendable-member center 14 and the linear member 3b and the distance sb between the linear member 3b and the rotation center axis 15b of the support member 5b satisfy the following equation:

$$rb<sb \qquad (15)$$

FIFTH EXAMPLE

Figures 13A, 13B:
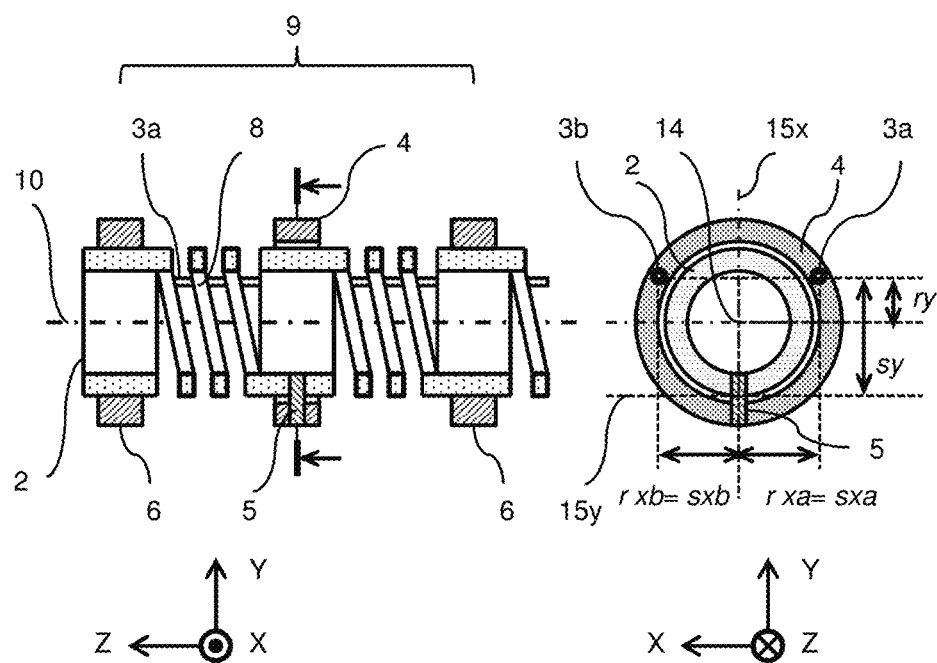
FIG. 13(A) illustrates a fifth example of the present disclosure.
FIG. 13(B) is a sectional view of FIG. 9(A) at the marked line.

Referring to FIG. 13, an arrangement of the linear members 3, the guiding members 4, and the support member 5 according to a fifth example of the present disclosure will be described.

The left side of FIG. 13 shows a sectional view of the region around the guiding members 4 taken along the YZ plane. The right side of FIG. 13 shows a sectional view of each guiding member 4. In FIG. 12, the elastic connecting portions 8a and 8b, which are respectively bendable along the YZ plane and the XZ plane, are alternately arranged in the bendable member 2. In contrast, the elastic connecting portions 8 illustrated in FIG. 13 are, for example, coil springs, and are structured so as to be bendable along any plane including the Z-axis. In this case, a bending component along the YZ plane direction and a bending component along the XZ plane direction may be discussed individually.

The guiding members 4 are supported on the bendable member 2 by the support member 5 so as to be rotatable around both the X-axis and the Y-axis. The bendable section 9 is bendable along any plane including the Z-axis by using the linear member 3a and the linear member 3b fixed to the distal end members 6.

When the bendable section 9 is bent along the XZ plane, the guiding member 4 is rotated around a rotation center axis 15x. In this case, the distance rxa between the bendable-member center 14 and the linear member 3a, the distance rxb between the bendable-member center 14 and the linear member 3b, the distance sxa between the linear member 3a and the rotation center axis 15x, and the distance sxb between the linear member 3b and the rotation center axis 15x satisfy the following relationships:

$$rxa=sxa \qquad (16)$$

$$rxb=sxb \qquad (17)$$

When the bendable section 9 is bent along the YZ plane, the guiding member 4 is rotated around a rotation center axis 15y. In this case, the distances from the bendable-member center 14 to the linear members 3*a* and 3*b* are both ry, and the distances from the rotation center axis 15*y* to the linear member 3*a* and 3*b* are both sy. Here, the following relationship is satisfied:

$$ry < sy \tag{18}$$

In the above-described five examples, a linear member 3, a guiding member 4, and a support member 5 are arranged so that the distance r between the bendable-member center 14 and the linear member 3 and the distance s between the linear member 3 and the rotation center axis 15 of the support member 5 satisfy the following expression:

$$r \le s \tag{19}$$

In this case, the radius of rotation of the guiding member 4 can be increased and the orientation error can be reduced. The numbers of linear members 3, guiding members 4, support members 5, bendable sections 9, etc., are not limited to those in the examples as long as they are designed so as to satisfy Expression (19).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A linear-member-driven manipulator comprising:
   a bendable member that is bendable along a bending plane and includes a plurality of bendable portions;
   a linear member used to bend at least one of the bendable portions;
   at least one guiding member that guide the linear member that is driven; and
   a plurality of support members, each support member extending from one of the guiding members to the bendable member,
   wherein the at least one guiding member is swingable with respect to the bendable member; and
   wherein, for each support member, a projection distance between the linear member and the support member on the bending plane is greater than or equal to a projection distance between the linear member and a bending neutral line of the bendable member on the bending plane.

2. The linear-member-driven manipulator according to claim 1, wherein the at least one guiding member includes guide holes through which one or more linear members extend.

3. The linear-member-driven manipulator according to claim 1, wherein each of the plurality of support members are at least one of a twistable structure, a flexible structure, and a structure including a pin in a sliding portion.

4. The linear-member-driven manipulator according to claim 3, wherein the twistable structure twists around an axis perpendicular to the bending plane.

5. The linear-member-driven manipulator according to claim 3, wherein the flexible structure bends so that the at least one guiding member swings along an axis parallel to the bending plane.

6. The linear-member-driven manipulator according to claim 3, wherein the structure including a pin in a sliding portion rotates around an axis perpendicular to the bending plane.

7. The linear-member-driven manipulator according to claim 1, wherein each bendable portion of the bendable member includes at least one distal end member to which the linear member is fixed.

8. The linear-member-driven manipulator according to claim 7, further comprising:
   a plurality of linear members, each fixed to the at least one distal end of one of the plurality of bendable portions.

9. The linear-member-driven manipulator according to claim 7, wherein at least one of the plurality of bendable portions includes at least one guiding member between two consecutive distal ends.

10. The linear-member-driven manipulator according to claim 1, wherein the support member is a super-elastic material.

11. The linear-member-driven manipulator according to claim 1, wherein the bendable portions of the bendable member are capable of being independently driven by a plurality of the linear members.

12. The linear-member-driven manipulator according to claim 1, wherein the bendable portions of the bendable member are bendable along more than one bending plane.

13. The linear-member-driven manipulator according to claim 1, wherein the bendable portions of the bendable member are independently bendable along different bending planes.

14. The linear-member-driven manipulator according to claim 1, wherein the at least one guiding member comprises a plurality of concentric ring-shaped portions.

15. The linear-member-driven manipulator according to claim 1, wherein the at least one guiding member comprises a plurality of concentric ring-shaped portions and a plurality of elastic connecting portions.

16. The linear-member-driven manipulator according to claim 1, wherein the at least one guiding member and the bendable member are supported by at least one of a twistable structure, a flexible structure, and a structure including a rotational sliding portion.

* * * * *